US010520462B1

(12) United States Patent
Eissa et al.

(10) Patent No.: US 10,520,462 B1
(45) Date of Patent: Dec. 31, 2019

(54) ELECTROCHEMICAL SCREENING FOR THE SELECTION OF DNA APTAMERS

(71) Applicant: Alfaisal University, Riyadh (SA)

(72) Inventors: Shimaa Eissa, Riyadh (SA);
Mohammed Zourob, Riyadh (SA);
Raja Chinnappan, Riyadh (SA);
Ayesha Siddiqua, Riyadh (SA)

(73) Assignee: Alfaisal University, Riyadh (SA)

( * ) Notice: Subject to any disclaimer, the term of this patent is extended or adjusted under 35 U.S.C. 154(b) by 0 days.

(21) Appl. No.: 16/199,174

(22) Filed: Nov. 24, 2018

(51) Int. Cl.
| | | |
|---|---|---|
| *C12Q 1/68* | (2018.01) | |
| *G01N 27/327* | (2006.01) | |
| *C12Q 1/686* | (2018.01) | |
| *C12Q 1/6806* | (2018.01) | |
| *C12N 15/115* | (2010.01) | |
| *G16B 30/00* | (2019.01) | |

(52) U.S. Cl.
CPC ....... *G01N 27/3275* (2013.01); *C12N 15/115* (2013.01); *C12Q 1/686* (2013.01); *C12Q 1/6806* (2013.01); *G01N 27/3273* (2013.01); *G16B 30/00* (2019.02)

(58) Field of Classification Search
None
See application file for complete search history.

(56) References Cited

U.S. PATENT DOCUMENTS

2016/0128321 A1* 5/2016 Bourdelais ............. A01N 25/00
504/358

OTHER PUBLICATIONS

Eissa, S., et al. Aptamer-based competitive electrochemical biosensor for brevetoxin-2. Biosensors and Bioelectronics, Vool. 69, p. 148-154, 2015.*
Yang, Kyung-Ae, et al. High-affinity nucleic-acid-based receptors for steroids. ACS Chem.biol., vol. 12, p. 3103-3112, 2017.*
Ti-Hsuan Ku et. al. Nucleic Acid Aptamers: An Emerging Tool for Biotechnology and Biomedical Sensing.
Song S. et.al. Aptamer-based biosensors, Trends in Analytical Chemistry, vol. 27, No. 2, 2008.
Maureen McKeague et.al. Challenges and Opportunities for Small Molecule Aptamer Development, Journal of Nucleic Acids vol. 2012, Article ID 748913, 20 pages.
Ruscito A et. al. Small-Molecule Binding Aptamers:Selection Strategies,Characterization,and Applications, Frontiers in Chemistry, May 2016|vol. 4|Article14.
Blind M et.al. Aptamer Selection Technology and Recent Advances,Molecular Therapy—Nucleic Acids (2015)4, e223.
Subash Chandra Bose Gopinath, Methods developed for SELEX,Anal Bioanal Chem (2007) 387:171-182.
Shaun D. Mendonsa et.al. In Vitro Evolution of Functional DNA Using Capillary Electrophoresis, J. Am. Chem. Soc. 2004, 126, 20-21.
Maxim Berezovski et.al. Nonequilibrium Capillary Electrophoresis of Equilibrium Mixtures: A Universal Tool for Development of Aptamers, J. Am. Chem. Soc. 2005, 127, 3165-3171.
Meng Jing et.al. Tracking the Emergence of High Affinity Aptamers for rhVEGF165 During Capillary Electrophoresis-Systematic Evolution of Ligands by Exponential Enrichment Using High Throughput Sequencing , Anal. Chem. 2013, 85, 10761-10770.
Jinpeng Wang et.al. Particle Display: A Quantitative Screening Method for Generating High-Affinity Aptamers, Angew. Chem. Int. Ed. 2014, 53, 4796-4801.
Marie-Sophie L. Raddatz et.al. Enrichment of Cell-Targeting and Population-Specific Aptamers by Fluorescence-Activated Cell Sorting, Angew. Chem. 2008, 120, 5268-5271.
Qing Wang, Screening of DNA Aptamers against Myoglobin Using a Positive and Negative Selection Units Integrated Microfluidic Chip and Its Biosensing Application, Anal. Chem. 2014, 86, 6572-6579.
Meng Jing, Isolation of DNA aptamers using micro free flow electrophoresis, Lab Chip, 2011, 11, 3703.
Glen Hybarger, A microfluidic SELEX prototype, Anal Bioanal Chem (2006) 384: 191-198.
Chen-Hsun Weng et.al. Screening of Aptamers on Microfluidic Systems for Clinical Applications, Sensors 2012, 12, 9514-9529.
Seung Soo Oh et. al. Improving Aptamer Selection Efficiency through Volume Dilution, Magnetic Concentration, and Continuous Washing in Microfluidic Channels, Anal. Chem. 2011, 83, 6883-6889.
Xinhui Lou et.al. Micromagnetic selection of aptamers in microfluidic channels, PNAS, Mar. 3, 2009, vol. 106, No. 9, 2989-2994.
Hsien-Chih Lai, et. al. Influenza A virus-specific aptamers screened by using an integrated microfluidic system, Lab Chip, 2014, 14, 2002.
Shao-Li Hong et. al. Multifunctional Screening Platform for the Highly Efficient Discovery of Aptamers with High Affinity and Specificity, Anal. Chem. 2017, 89, 6535-6542.
Xiaohui Liu et. al. Selection of aptamers based on a protein microarray integrated with a microfluidic chip, Lab Chip, 2017, 17, 178.
Nesrine Aissaoui et. al. Catalytic activity and thermostability of enzymes immobilized on silanized surface: Influence of the crosslinking agent, Enzyme and Microbial Technology 52 (2013) 336-343.
Henrik H. J. Persson, et. al. Versatile Method for Chemical Reactions with Self-Assembled Monolayers of Alkanethiols on Gold, Langmuir 2001, 17, 3643-3650.

(Continued)

*Primary Examiner* — Suryaprabha Chunduru
(74) *Attorney, Agent, or Firm* — Geeta Kadambi; Riddhi IP LLC

(57) ABSTRACT

An electrochemical screening method for the selection of DNA aptamers against 11-deoxycortisol (11-DCL) using gold electrode for target immobilization is described. The gold electrode is used as solid matrix instead of the beads for SELEX. The selection steps (SELEX) are performed on the 11-DC modified electrode directly as the DNA library in the first round or the enriched DNA pools in the subsequent rounds were incubated on the electrode, then the unbound DNA is washed and the bound DNA is measured directly by square wave voltammetry. Then elution of the bound DNA is performed for further use.

6 Claims, 11 Drawing Sheets

Specification includes a Sequence Listing.

(56) References Cited

OTHER PUBLICATIONS

Shimaa Eissa et. al. Aptamer-basedcompetitiveelectrochemicalbiosensorforbrevetoxin-2, Biosensors and Bioelectronics 69 (2015)148-154.
V. A. Simossis et. al. Homology-extended sequence alignment, Nucleic Acids Research, 2005, vol. 33, No. 3, p. 816-824.
Kyung-Ae Yang et. al. High-Affinity Nucleic-Acid-Based Receptors for Steroids, ACS Chem. Biol. 2017, 12, 3103-3112.

* cited by examiner

FIG. 7

ELECTROCHEMICAL SCREENING FOR THE SELECTION OF DNA APTAMERS

CROSS REFERENCE TO RELATED FILES

The current application is submitted with a sequence file RIPLLC032.009US1_ST25 created on Nov. 24, 2018 and the size is KB.

FIELD OF TECHNOLOGY

This application discloses electrochemical screening method for the selection of DNA aptamers against 11-deoxycortisol (11-DCL) using gold electrode for target immobilization.

BACKGROUND OF INVENTION

Aptamers are single stranded DNA or RNA molecules that have emerged as a new class of bio-receptors that are analogous to antibodies in terms of binding to their target with high affinity and specificity. Aptamer sequence is capable of forming a unique 3D structure owing to the presence of the intramolecular attractions between the nucleotides such as van der waals, hydrogen bonding and hydrophobic interactions (Ku T. H. 2015). Aptamers have been identified for several analytes such as proteins, viruses, toxins, drugs, hormones, bacteria, metal ions, peptides, cells, ions and even tissues with high affinity that can reach picomolar dissociation constant ($K_d$). They have shown several advantages over antibodies which make them better candidates for many affinity-based applications, particularly in the development of biosensors (Song, S. et. al. 2008).

Aptamers are selected by an in vitro process which does not require the use of experimental animals, thus, it is possible to acquire aptamers for both toxic and non-immunogenic molecules. Indefinite number of aptamers can be made easily and at low cost once the aptamer for the target is identified and its sequence is obtained. Aptamers have high thermal stability and can be effortlessly modified by numerous chemical tags with negligible effect on their binding affinity and specificity allowing them to be easily immobilized on different solid supports. However, despite the advantages and the great promise of aptamers in different therapeutic and diagnostic applications, yet limited number of aptamers has been successfully identified, particularly for small molecules (McKeague, M et. al. 2012, Ruscito, A et. al. 2016). This is majorly attributed to the limitation of the conventional selection process of the aptamers known as Systematic Evolution of Ligands by Exponential enrichment (SELEX). The SELEX process usually involves two major steps: multiple iterative rounds of selection (10-20) from a pool of large library of DNA sequences and then amplification of the selected subpool. In each round the DNA library is incubated with the target immobilized on solid matrix (usually sugar based or magnetic microbeads). Then, several washing steps for the unbound DNA is performed followed by elution, PCR amplification of the bound DNA and then purification of the single stranded DNA pool for further rounds. Moreover, the evaluation of the aptamer enrichment is usually done by monitoring the fluorescence of the eluted DNA after each round. Thus, the SELEX process is expensive, labor intensive, time consuming and sometime inefficient.

In order to overcome these limitations, some innovative selection methods have been developed over the last 20 years combining various techniques to accelerate and improve aptamers selection (Gopinath 2007; Blind and Blank 2015). Capillary electrophoresis (CE)-SELEX (Mendosa S D et. al. 2004, Berezovski M et. al. 2005) and nitrocellulose filter binding SELEX (Blind, M et. al. 2015) have been reported. However, these methods can be only used for large molecules such as proteins. Flow cytometry-SELEX and fluorescence-activated cell sorting-SELEX (Raddatz, Dolf et al. 2008; Wang, Gong et al. 2014) have been also developed for selecting aptamers against cells. Microfluidic technologies (Hybarger, Bynum et al. 2006; Jing and Bowser 2011; Weng, Huang et al. 2012; Wang, Liu et al. 2014; Hung, Wang et al. 2016) have been also integrated with different SELEX methods such as CE (Berezovski, Drabovich et al. 2005), sol-gel and magnetic beads (Lou, Qian et al. 2009; Oh, Ahmad et al. 2011; Lai, Wang et al. 2014) in order to increase the separation efficiency. However, in these methods, the aptamer enrichment is not monitored in real-time leading to selection blindness, longer selection time and higher number of failure selection trials (Hong, Wan et al. 2017; Liu, Li et al. 2017). Therefore, it is highly demanded to develop a rapid and low cost selection approach that possesses real-time evaluation capability and remarkable efficiency.

SUMMARY

The application discloses several embodiments for performing an electrochemical screening method for an aptamer. The electrochemical screening is performed on a target immobilized electrode surface by selecting aptamers from a library of single stranded DNA. In one embodiment a method of making an immobilized surface made up of metal, dielectric polymer or conductive polymer is disclosed. In another embodiment, selection of aptamers is performed after the electrochemical screening done for a specific target.

In one embodiment, immobilizing a target sequence on an electrode by the following steps:
a) coating an electrode with a cysteamine hydrochloride to create a cysteamine-modified electrode, wherein the electrode is at least one of a metal, dielectric polymer and conductive polymer; b) washing the cysteamine-modified electrode with an ethanol to remove an unbound cysteamine hydrochloride from the cysteamine-modified electrode; c) adding a cross linker 1, 4-phenylene diisocyanate to an amine group of cysteamine hydrochloride on the surface of the cysteamine-modified electrode; d) washing with a methanol to remove any unbound cross linker 1, 4-phenylene diisocyanate from the surface of the cysteamine-modified electrode; and e) incubating the cysteamine-modified electrode in a 11-deoxycortisol solution for crosslinking a 11-deoxycortisol molecule on the surface of the cysteamine-modified electrode to create a 11-deoxycortisol-modified electrode to perform an electrochemical selection of the aptamer.

In another embodiment, the method further comprises using a synthetic single stranded DNA oligonucleotide sequence to be incubated with the 11-deoxycortisol-modified electrode; measuring the square wave volatmmetry reduction peak current of the electrode in a ferro/ferricyanide redox solution; binding the single stranded DNA oligonucleotide sequence to the 11-deoxycortisol-modified electrode by immersing in binding buffer; washing the electrode and measuring the square wave volatmmetry reduction current after binding; eluting a bound single stranded DNA from the 11-deoxycortisol-modified electrode using an eluting buffer; repeating binding and eluting steps multiple times to collect a single stranded eluted DNA sequence; and performing a polymerized chain reaction on the eluted single stranded DNA sequence to obtain a DNA product.

In yet another embodiment, the method further comprises cloning the DNA product on a specific vector and grown in an agar plates; selecting a single colony of and growing overnight in a liquid media for a colony to grow; performing polymerized chain reaction to amplify the single stranded DNA inserts using M13 forward and M13 reverse primers sites inside the specific vector to make the aptamer; sequencing all the aptamers obtained after amplification and aligning using specific software; and performing a binding analysis using the electrochemical screening method for 11-deoxycortisol with the aptamer. In one embodiment the metal is gold.

In one embodiment, aptamer is SEQ ID NO: 3-DC 3, SEQ ID NO: 4-D 28, SEQ ID NO: 5-DC 7, SEQ ID NO: 6 DC-13, SEQ ID NO: 7 DC-19, SEQ ID NO: 8 DC-21, SEQ ID NO: 9 DC-27, SEQ ID NO: 10 DC-15, SEQ ID NO: 11 DC-17, SEQ ID NO: 12 DC-23 and SEQ ID NO: 13 DC-14.

Other features will be apparent from the accompanying drawings and from the detailed description that follows.

BRIEF DESCRIPTION OF FIGURES

Example embodiments are illustrated by way of example and not limitation in the figures of the accompanying drawings, in which like references indicate similar elements and in which:

FIG. 7 shows the multiple sequence alignment analysis of the selected aptamers using PRALINE program.

Figure 1A:
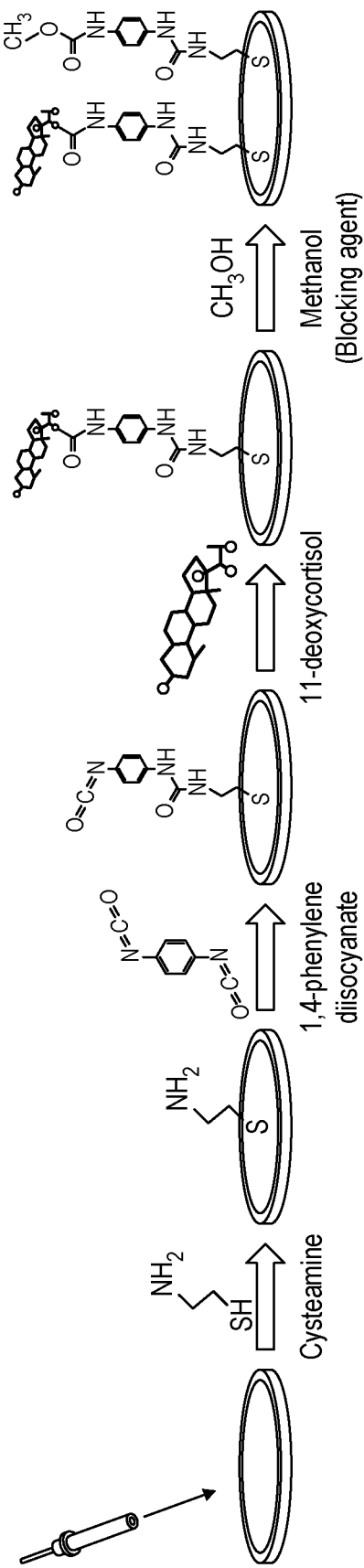
FIG. 1A: Shows the immobilization of 11-deoxycortisol on the gold electrode surface.
Figure 1B:
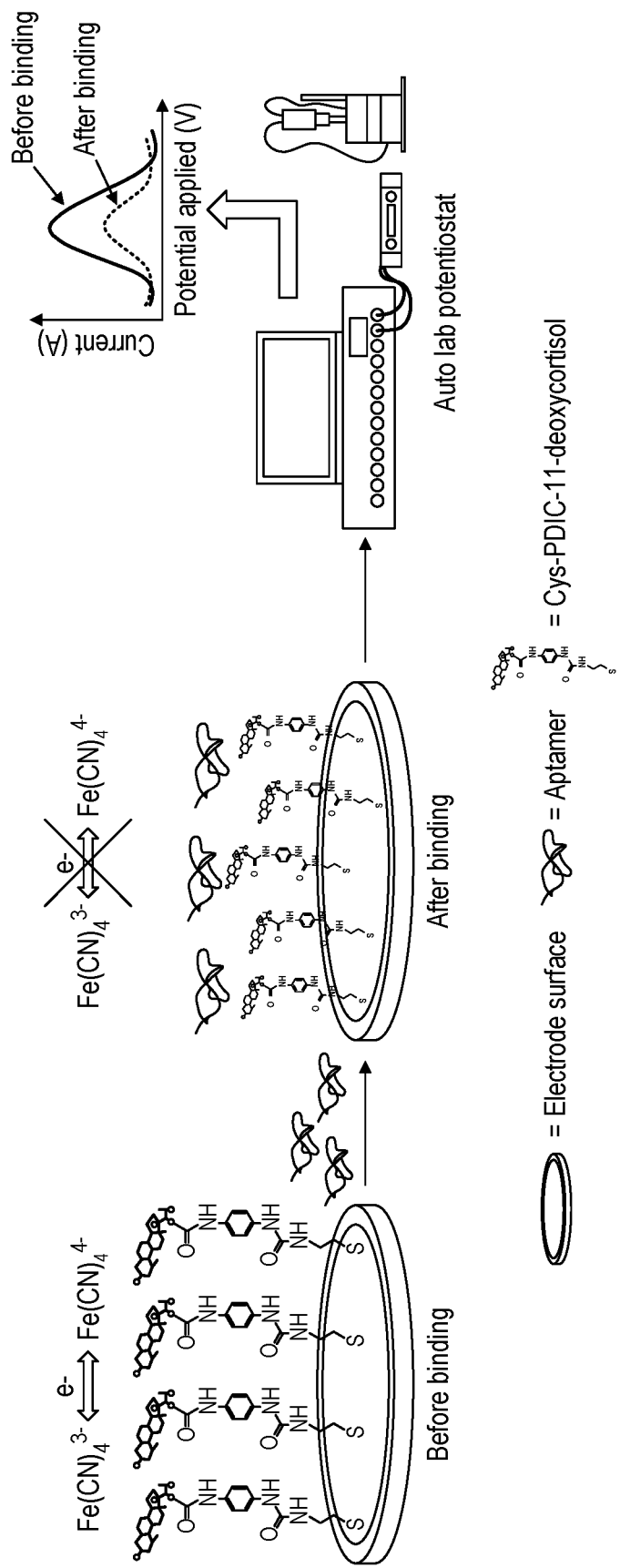
FIG. 1B shows Label-free voltammetric monitoring of the bound DNA.

Other features of the present embodiments will be apparent from the accompanying drawings and from the detailed description that follows.

DETAILED DESCRIPTION

The instant application describes a novel electrochemical-based SELEX method for efficient low-cost and rapid selection of DNA aptamers. In our electrochemical-based SELEX, the target analyte is covalently immobilized on gold electrode surface. The interaction of the single stranded DNA library and the target-modified electrodes can be directly monitored voltammetrically by measuring the current of the electrodes in ferro/ferricyanide redox couple. The non-bound or weakly bound sequences can be easily and effectively removed through a washing process within 1 min. The platform is used to perform the negative and positive selection in order to improve the specificity of the selection. Compared to the conventional SELEX, the electrochemical-SELEX approach can eliminate the need of DNA labelling which significantly reduces the cost of the procedure. Moreover, the use of electrodes as solid matrix for target immobilization reduces the time of the washing and elution steps and allows efficient control of the selection via the label-free, in-situ and real-time monitoring of the enrichment process.

In one embodiment, the use of 11-deoxycortisol (11-DCL) hormone as a small molecule target is disclosed. 11-deoxycortisol is a hormone that is converted to cortisol by an enzyme called 11ß-hydroxylase. Thus, the detection of 11-DCL in blood is used to diagnose 11ß-hydroxylase and other adrenal gland abnormalities. After eight round of selection, high affinity and specificity aptamers against 11-DCL were obtained showing dissociation constants in the sub- to low nanomolar level. One of the selected aptamers has been successfully used to develop a volatmmetric competitive aptasensor for 11-DCL shows high sensitivity and possible applicability to serum samples. The instant method paves the way for rapid, simple, low cost, highly efficient selection of aptamers against various targets including small molecules.

Experimental Method

Materials and Reagents:

11-deoxycorticol, cortisol, corticosterone and pregnenolone were purchased from cerilliant (Texas, United States). Potassium chloride, potassium ferrocyanide ($K_4Fe(CN)_6$), potassium ferricyanide ($K_3Fe(CN)_6$), phosphate-buffered saline: pH 7.4 (PBS), cysteamine hydrochloride, sulphuric acid ($H_2SO_4$), hydrogen peroxide ($H_2O_2$), hydrochloric acid (HCl), 1,4-phenylene diisocyanate (PDIC), toluene, sodium chloride (NaCl), magnesium chloride ($MgCl_2$), Acrylamide/bisacrylamide (30% solution), urea, tris-base, boric acid, EDTA disodium dehydrate (to prepare TBE buffer), Tetramethylethylenediamine (TEMED) and ammonium persulfate (APS), ethanol, methanol and mercaptohexanol (MCH) were purchased from Sigma Aldrich (St Louis, Mo., USA). The ssDNA library, labeled and unlabeled primers for PCR amplification, aptamer sequences were custom-manufactured by Metabion International (Plangg, Germany). Taq plus polymerase, Taq Buffer, DNTPs for PCR and a 100-base pair ladder was bought from ACE Biotech (Riyadh, Saudi Arabia). Agarose powder and 50× Tris base, acetic acid and EDTA buffer (TAE buffer) for performing agarose gel electrophoresis were obtained from Bio-Rad (California, United States). Amicon Ultra-0.5 mL centrifugal desalting filter units with a 3 kDa molecular cut-off filter were acquired from EMD Millipore (Alberta, Canada). The binding buffer which is used during the incubation and washing steps of the aptamer selection is prepared by mixing 50 mM Tris, pH 7.5, 150 mM NaCl and 2 mM $MgCl_2$. The elution buffer used for eluting the target bound aptamer sequences is 7 M urea in binding buffer. The ssDNA is eluted from the denaturing gel by using Tris-EDTA buffer (TE) that is prepared by 10 mM Tris (pH 7.4) and 1 m M EDTA. A homogeneous mixture of 1,4-phenylene diisocyanate (PDIC) solution was prepared by dissolving PDIC in toluene by ultrasonicating for 30 min. Milli-Q water was used to prepare all the solutions. TOPO TA Cloning Kit consisting of the pCR2.1-TOPO vector and the *E. coli* competent cells were purchased from Invitrogen Inc. (New York, USA).

Instrumentations: Auto lab PGSTAT302N (Eco Chemie, The Netherlands) potentiostat/galvanostat was used to carry out all electrochemical measurements in this study. The potentiostat was connected to a computer and controlled by a Nova 1.11 software. For all the electrochemical measurements, a standard three electrode system was used. The working electrode was a conventional solid gold electrode, Ag/AgCl was used a reference electrode and a Pt wire was used as a counter electrode.

The Polymerase Chain Reaction (PCR) was carried out using a thermocycler purchased from Eppendorf (Westbury, N.Y., USA). The Fluorescence measurements were carried out using Nano Drop 3300 Fluorospectrometer and the UV quantification measurements were performed using Nano Drop 2000C Spectrophotometer purchased from Fisher Scientific, Canada.

Immobilization of 11-deoxycortisol on the gold electrode: Prior to immobilization, the solid gold electrodes (2 mm in diameter) were manually polished on two different polishing surfaces, each for seven minutes. Micro polish II alumina with a particle size of 1.0 µm was used to polish the electrode on the first surface (nylon pad) and then master prep polishing suspension with a particle size of 0.05 µm was used to polish the electrode on the second surface. This was then followed by the rigorous washing of the electrodes with Milli-Q water and ethanol. In order to remove hydrocarbon contaminants, the electrodes were further cleaned in piranha solution which consists of concentrated $H_2SO_4$ and chilled $H_2O_2$ (3:1 v/v). The electrodes were immersed in the piranha solution for 90 s and then cleaned meticulously with double distilled water. Next, the electrodes were cleaned electrochemically in 0.1 M $H_2SO_4$ for 5 min with a scan rate of 100 mV/s, cycling in the potential range of −0.2 and 1.6 V for 30 cycles, followed by rinsing with distilled water and ethanol and then immersion in ethanol until further use.

After polishing the electrodes, an aqueous solution of 10 mM cysteamine hydrochloride was prepared. The pretreated gold electrodes were incubated in this solution for 2 h at room temperature. After that, the electrodes were washed with absolute ethanol to remove any unbound cysteamine residues and then dried. The cysteamine-modified electrodes (Cys/Au) were then immersed in 6.5 mM solution of 1,4-phenylene diisocyanate (PDIC) for 2 h at room temperature. Next, the electrodes were washed with dimethyl formamide to remove any PDIC residues and then dried. 1.0 mg/ml of 11-DCL in methanol was immediately added on the surface of the electrode and incubated for 2 hours at room temperature. After that, the electrodes were rinsed with methanol to remove any unbound 11-DCL. The electrodes were then incubated in methanol for 5 h to block any remaining free isocyanate groups (FIG. 1A). The 11-DCL-coupled electrodes were then washed with 0.1 M Tris buffer (pH 7.5) and stored at 4° C. in Tris buffer until further use.

Electrochemical measurements: All the electrochemical measurements were carried out at room temperature in 5 mM ferro/ferricyanide $[Fe(CN)_6]^{3-/4-}$ solution prepared in PBS buffer, pH 7.4 (1:1 molar ratio). The square wave voltammetry measurements were carried out using an autolab potentiostat at a scan rate of 125 mV/s and within the potential range of 0.4 V to −0.2 V. The parameters for SWV measurements were as follows: a frequency of 25 Hz, time interval of 0.04 s, amplitude of 20 mV and a step potential of 5 mV. For the SWV detection graphs, baseline correction was performed. The cyclic voltammetry (CV) measurements were carried out at a scan rate of 100 mV/s in the potential range of −0.2 to 0.5 V. The electrochemical impedance spectroscopy (EIS) was recorded within a frequency range of $10^4$ to 0.1 Hz, AC amplitude of 10 mV and a DC potential of +0.20 V. Modified Randles equivalent circuit was applied to fit the impedance spectra.

Figure 2:
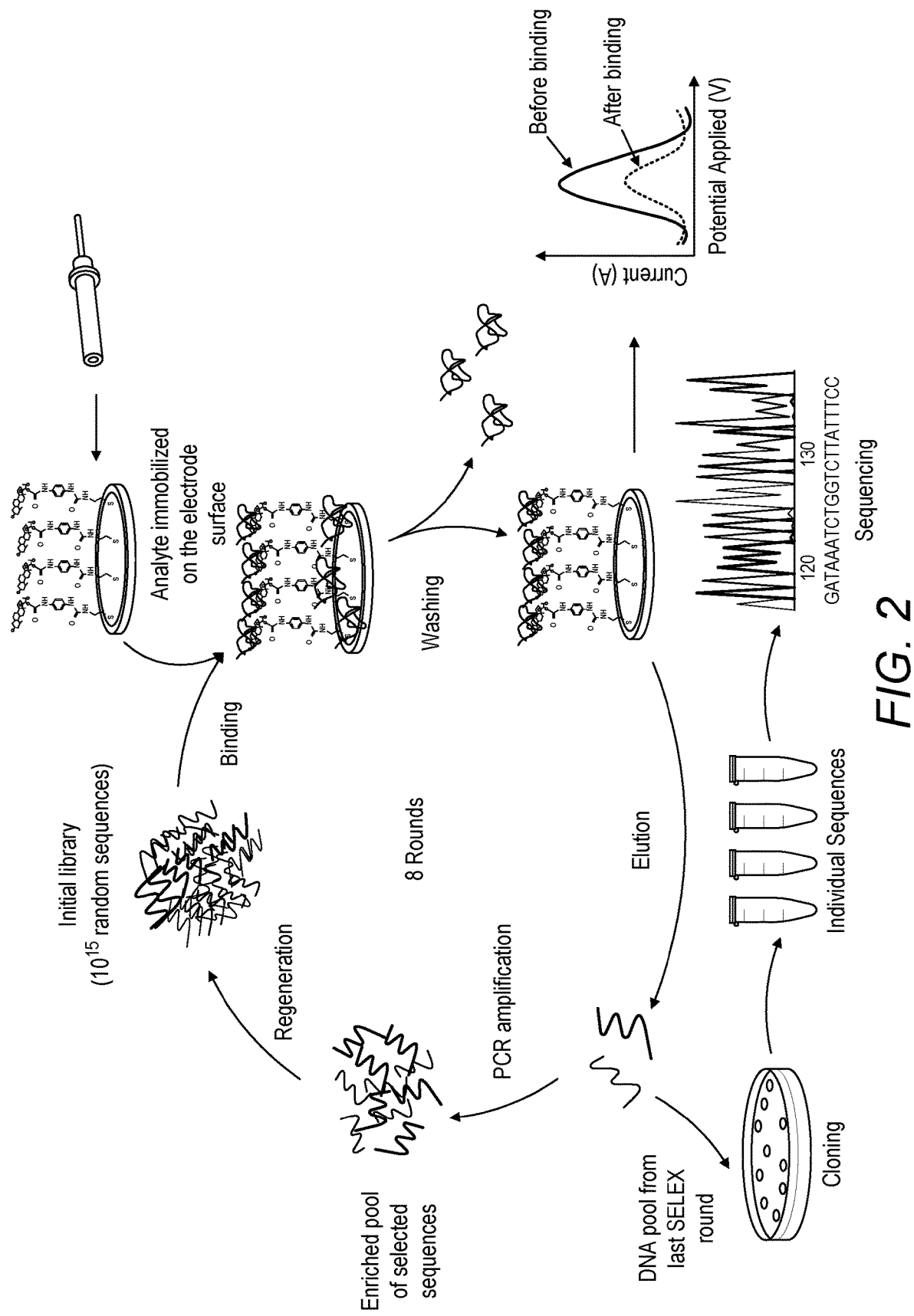
FIG. 2. shows Overview of the electrochemical Systematic evolution of ligands by exponential enrichment (SELEX) protocol using electrode that is prior art.

In Vitro selection of the aptamers for 11-deoxycortisol: A diagram of the SELEX process used to select aptamers for 11-DCL is described in FIG. 2. In this process, 11-DCL was immobilized on the surface of gold electrode and then exposed to a ssDNA library pool. For this purpose, a chemically synthesized random ssDNA library ($10^{15}$ sequences) was utilized. This oligonucleotide library comprises of a medial random region of 60 nucleotides, flanked by two constant regions of primer binding sites (18-nucleotide sequences) for PCR amplification, at the 3' and 5' ends (SEQ ID NO:1, 5'-ATACCAGCTTATTCAATT-N60-AGA-TAGTAAGTGCAATCT-3' SEQ ID NO:2).

Prior to incubating the electrode with the ssDNA library, the SWV reduction current of the 11-DCL modified electrode is measured in ferro/ferricyanide solution. For the first cycle, 3 nmol concentration of ssDNA library in binding buffer was heated at 95° C. for 5 min, then cooled at 4° C. for 10 min and then kept at 25° C. for 5 min. Next, the electrodes were incubated with the treated ssDNA library for 2 h. After that, the electrodes were washed with aliquots of binding buffer for three times. Then, the SWV reduction current of the electrode is measured again in ferro/ferricyanide solution. The elution buffer was then heated at 40° C. and the electrodes were incubated in 200 µl aliquots of elution buffer for five times for a time interval of 10 min. After that, the eluted DNA is collected and added to an ultrafiltration device (3 KDa cut-off filters) and then desalted with water for 6 times. Starting from the second cycle, the fluorescence of the eluted DNA was measured by Nano drop fluorospectrophotometer after each round for a comparison purpose. Negative selection was performed after five rounds of SELEX, in which the electrode surface was modified with the linkers, blocked and then incubated with the DNA pool in the absence of the target (negative electrode). Next, the washes were collected and desalted and then subjected to heating and cooling treatment, then incubated with the positive electrode (immobilized with the target) and the cycle was continued. The ssDNA pool selected after each round was amplified by PCR in 23 equivalent reaction tubes consisting of 50 μl reaction mixture. Each tube consisted of 2 units of Taq Plus and polymerase buffer, 2 mM $MgCl_2$, 200 μM dNTP, 0.2 μM of forward and reverse primers. The forward primer is modified with fluorescein isothiocyanate (FITC) fluorophore label in order to enable the fluorescence measurement for comparison with the electrochemical measurements SEQ ID No: 1 (forward primer: 5'-fluorescein-ATACCAGCTTATTCAATT-3'), whereas the reverse primer is modified with hexaethylene glycol linker followed by a long poly A chain SEQ ID No: 2 (reverse primer: 5'-polydA20-PEG6-AGATTGCACTTACTATCT-3'). The PCR was carried out at the following conditions; 94° C. for 10 min, subsequently followed by 25 cycles of 94° C. for 1 min, 47° C. for 1 min, 72° C. for 1 min, and a last extension step of 10 min at 72° C. The volume of the PCR product was reduced by performing ethanol precipitation. To the PCR product, 3M sodium acetate and 100% chilled ethanol were added. This mixture was vortexed thoroughly, then kept at −80° C. for 1 h and then centrifuged at 13,000 rpm for 30 min After centrifugation, the supernatant is discarded, and the pellet is allowed to dry to remove any traces of ethanol. Next, the pellet is resuspended by adding water and formamide (1:2 v/v) and heated to 90° C. for 10 minutes. The desired ssDNA was separated from the dsDNA PCR product by using 12% denaturing PAGE. The fluorescent bands were cut from the gel and then added to TE buffer. The ssDNA is eluted by a freeze thaw cycle, in which the gel and TE buffer mixture was cooled at −80° C. for 30 min, then heated at 90° C. for another 30 min and then kept rotated overnight. The following day, the eluted ssDNA in TE buffer was concentrated, desalted by ultrafiltration device and then UV quantified for its use in the next selection round.

Figure 7:
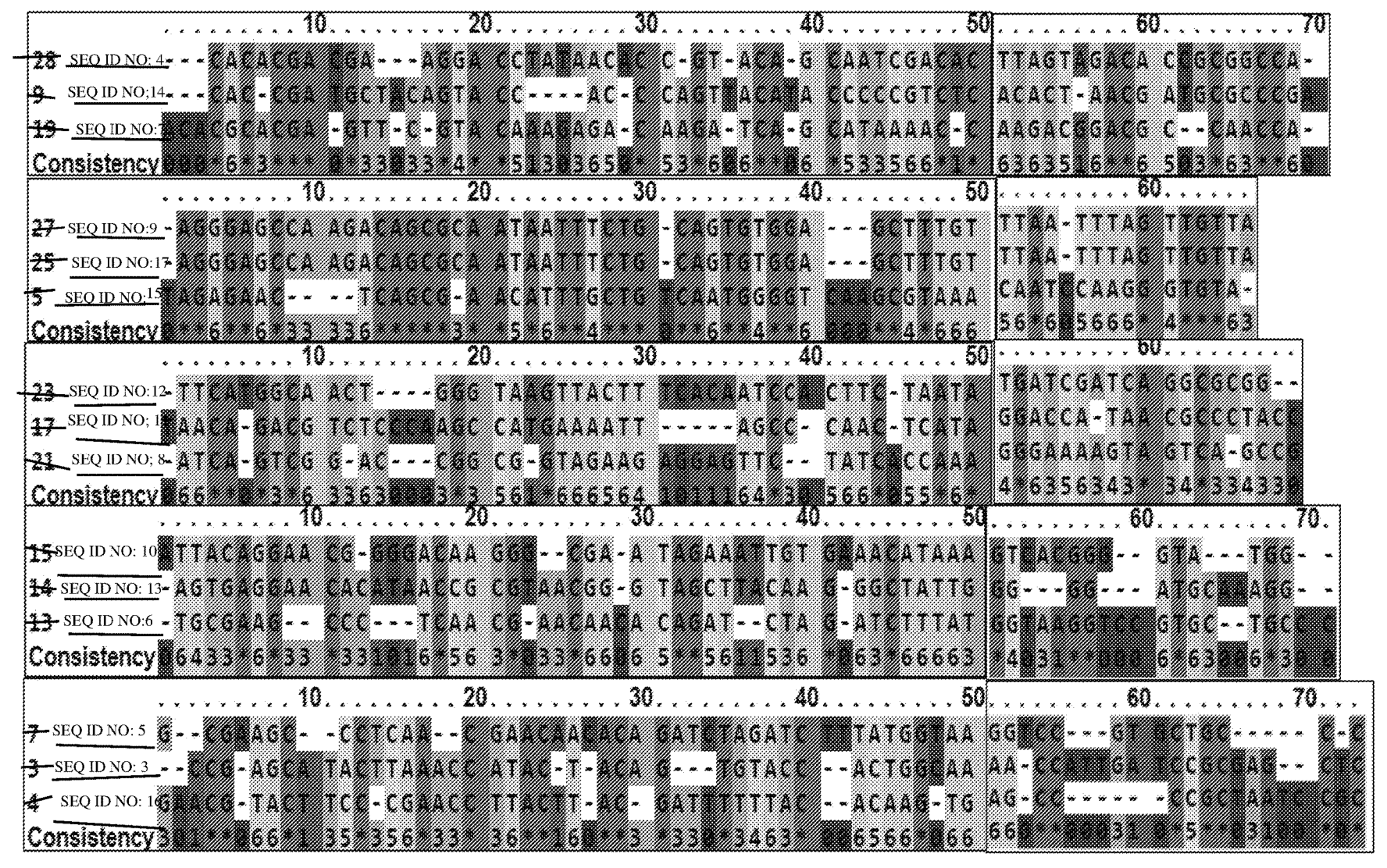

Cloning and Sequencing of the selected aptamers: After performing eight rounds of selection, the ssDNA obtained after the eighth round was amplified by PCR and then ligated to a pCR2.1-TOPO vector, using the TOPO TA Cloning Kit (Invitrogen). Next, LB-agar media supplemented with ampicillin was prepared and added to the Petri dishes. After the media dried, X-gal was added to the plates. The ligated product was added to the competent cells, kept on ice for 30 min, then subjected to heat chock for 30 s on a water bath (42° C.) and then back at ice for 1-2 min. Next, SOC media was added to the competent cells tube and the tube was kept rotated for 1 h at 37° C. After 1 h rotation, the cells were spread on the Petri dish and the colonies were allowed to grow overnight. Only white colonies were then picked up and allowed to grow in a liquid media overnight. Then, colony PCR was performed to amplify the ssDNA inserts using M13 forward and M13 reverse primers sites inside the vector. Finally, these inserts were sequenced and the sequences obtained were aligned using a specific software that is PRALINE™ (FIG. 7).

Dissociation constants determination of the identified aptamers to 11-deoxycortisol: After cloning, sequencing and alignment analysis of the selected sequences against 11-DCL, we picked up some sequences for binding study to determine their affinity to 11-DCL. The binding assay was performed by incubating different concentrations of each aptamer individually (1 to 50 nM) on 11-deoxycortisol-modified gold electrodes prepared as described above. After each incubation, the electrodes were washed and then the SWV was recorded. Then, the bound DNA to the electrode was monitored by calculating the percentage change in the peak current ((i°−i)/i° %). Saturation binding curves were plotted for each sequence and the dissociation constants ($K_d$) were determined by nonlinear regression analysis of the curves.

Electrochemical competitive aptasensor for 11-deoxycortisol-from the binding analysis, SEQ ID NO: 11-DC17 aptamer showed the highest affinity (lowest $K_d$) to 11-DCL, therefore, it was chosen to develop a competitive aptasensor. For the 11-DCL detection experiments, the 11-DC electrodes were incubated for 20 min with 5 nM SEQ ID NO: 11-DC17 aptamer mixed with specific concentrations of 11-DC. For the cross reactivity testing, similar experiment was performed using 1 ng/ml of cortisol, corticosterone or pregnenolone instead of 11-DCL. The electrodes were then washed with 0.1 M Tris buffer, pH 7.4 and subjected to SWV measurements.

Results and Discussion

Immobilization of 11-deoxycortisol on the gold electrodes: One of the most important steps in electrochemical-SELEX is the choice of the immobilization matrix of the small molecule target which allows efficient partitioning of the bound and unbound DNA. Here, we chose standard gold electrode as solid matrix for target immobilization because of its high conductivity, intrinsic stability, and capability of regeneration. The 11-DCL molecules were attached to the gold surface via their hydroxyl groups. The gold surface was first functionalized using 2 step process. First, cysteamine hydrochloride was incubated on the gold surface in order to form a self-assembled monolayer exposing a terminal amine groups. Then, the Cys/Au electrodes were incubated with PDIC cross linker. One of the isocyanate groups is used to react with the amine group of the cysteamine yielding carbamide moiety and the other binds to the hydroxyl group of the 11-DCL yielding carbamate (urethane) moiety (Persson, Caseri et al. 2001; Aissaoui, Landoulsi et al. 2013; Eissa, Siaj et al. 2015) (FIG. 1A). This linker was previously shown to be very efficient, highly stabile and has low toxicity. Finally, the unreacted cyanate groups were blocked with methanol to minimize any nonspecific adsorption.

Figure 3A:
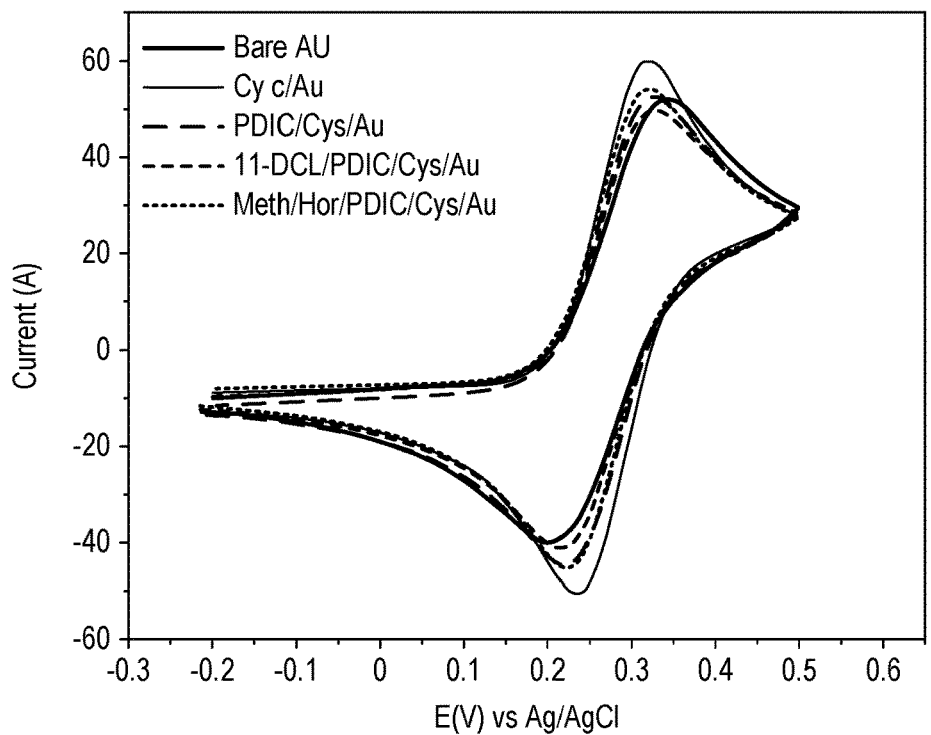
FIGS. 3A, 3B and 3C shows Cyclic voltammetry, SWV and Nyquist plots of 5 mM $[Fe(CN)_6]^{4-/3-}$ redox solution in PBS, pH 7.4, for the different modification steps of the electrode (the black curves are the bare Au electrode, Cys/Au (red), PDIC/Cys/Au (blue), 11-DCL/PDIC/Cys/Au (green) and Methanol/11-DCL/PDIC/Cys/Au (cyan). The scan rate of the CV was 100 mV/s and the EIS was carried out in a frequency range of $10^4$ to 0.1 Hz, AC amplitude of 10 mV and a DC potential of +0.20 V. The circuit applied to fit the impedance spectra is shown in the inset of FIG. 3C.
Figure 3B:
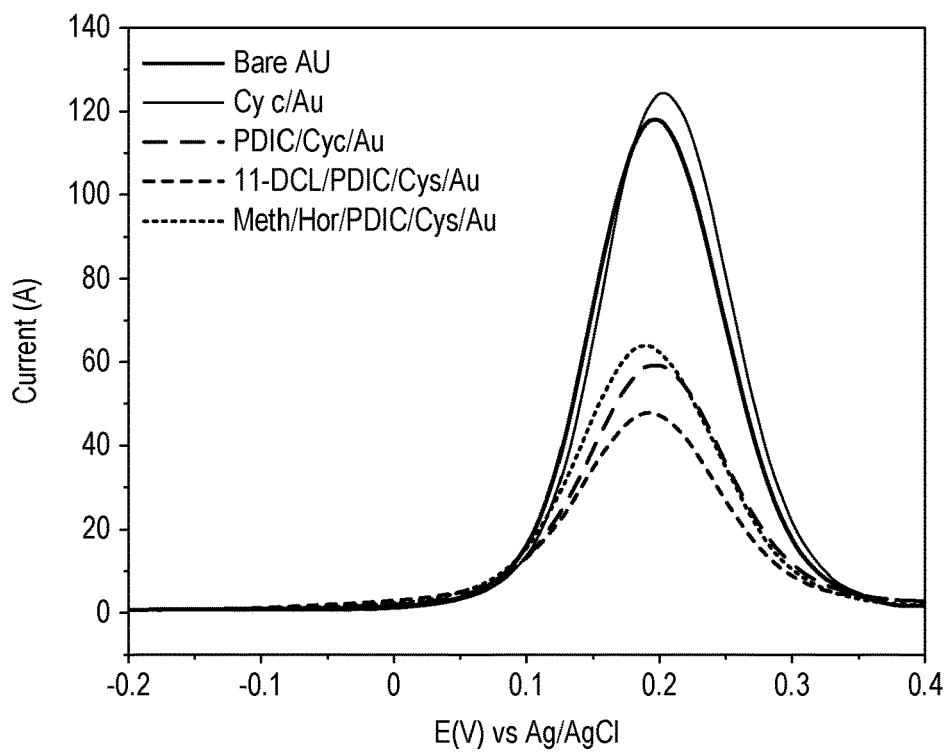

With the aim of confirming the success of the immobilization steps of the target on the electrode surface, we used CV and SWV as well as EIS measurements. FIG. 3A shows the cyclic voltammograms of the gold electrode before and after each modification step measured in $[Fe(CN)_6]^{3-/4-}$ redox couple solution in PBS buffer pH 7.4. The bare gold electrode showed the characteristic reversible CV behaviour of clean gold exhibiting well defined anodic and cathodic peaks with peak-to-peak separation (ΔE) of around 90 mV. The cysteamine-modified gold surface then showed a slight increase in the peak current and a decrease in the ΔE which is attributed to the positively charged amine groups of the cysteamine which attracts the redox anions indicating the successful formation of the self assembly monolayer. On the other hand, after the incubation with the PDIC linker, the anodic and cathodic peak currents slightly decreased again likely, due to the negative charge of the cyanate groups which repelled the $[Fe(CN)_6]^{3-/4-}$ molecules from the surface. However, after adding the 11-deoxycortisol to the modified electrodes, the peak current was further decreased indicating the successful attachment of the target molecules on the surface leading to retardation of the electron transfer. After blocking the surface with methanol, the current increased again due to the blocking of the remaining free negatively charged cyanate groups. Because only slight changes were seen using CV, we have also utilized SWV as a more sensitive technique for characterization. A shown in FIG. 3B, the SWV reduction peak of $[Fe(CN)_6]^{3-/4-}$ showed the same trend after each modification step with more pronounced differences in the peak currents.

Figure 3C:
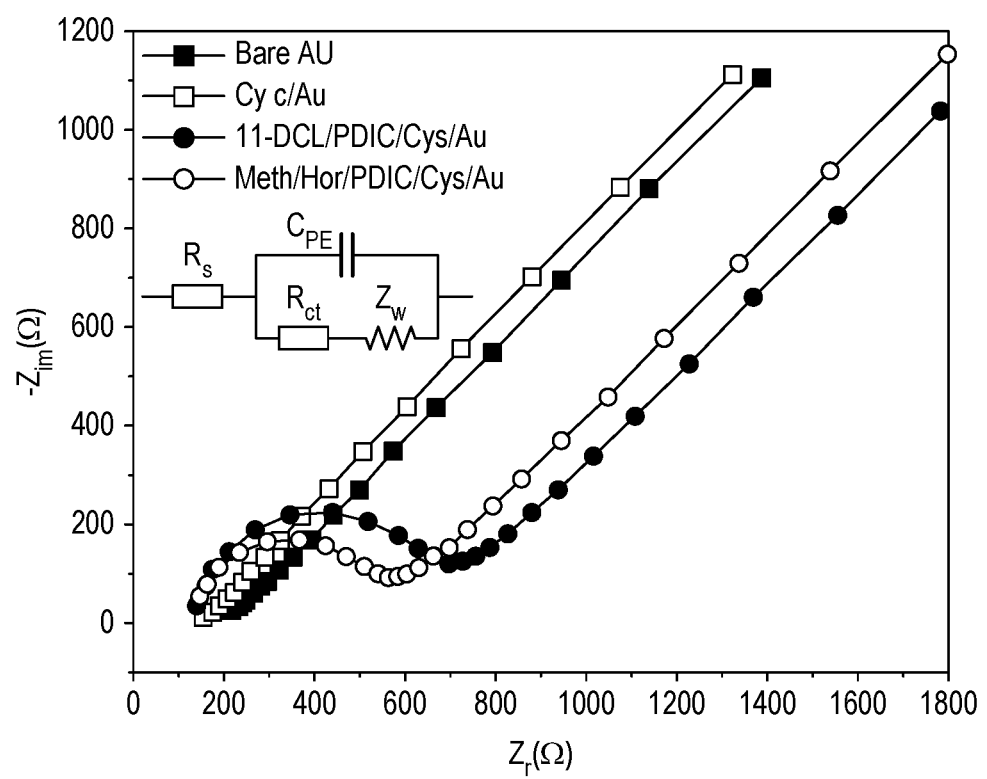

FIG. 3C, shows the EIS Nyquist plots of the electrodes after each modification step. Each spectrum consists of two parts: the semicircle part at high frequency and the straight line part at low frequency which corresponds to the electron transfer and diffusion processes, respectively. In order to fit the experimental data, we used modified Randles equivalent circuit (Inset of FIG. 3C) which consists of a charge-transfer resistance ($R_{CT}$), solution resistance ($R_S$), Warburg impedance ($Z_W$) that results from the diffusion of the redox couple from the bulk of the solution to the electrode interface and a constant phase element (CPE), representing the electrical double layer capacitance. Among the electrical parameters, $R_{CT}$ (represented by the diameter of the semicircle) is usually the parameter of choice used to characterize the modification of the electrode-solution interface. As shown in FIG. 3C, the bare gold electrode showed a small semicircle and a straight line indicating the fast electron transfer on the bare gold surface and thus, very low $R_{CT}$. The semicircle is decreased even more after the cysteamine modification due to the attraction of the amine groups to the redox anions leading to faster electron transfer process. However, after the activation with the linker and the attachment of the target, the resistance was dramatically increased due to the blocking effect of the target molecules. Then, slight increase in the $R_{CT}$ was observed after blocking the unreacted cyanate groups with methanol. Thus, the CV, SWV, and EIS results confirmed the successful immobilization of 11-deoxycortisol on the gold electrodes.

In Vitro selection of 11-deoxycortisol-binding aptamers: Here, we used a library which consists of $1.8 \times 10^{15}$ random 60-nucleotide sequences. Each SELEX cycle was performed as follow: 1) incubating the target electrode with the library, 2) simple washing of the electrodes for 3 times each for 30 s, 3) Elution of the bound DNA to the electrodes, 4) desalting and PCR amplification of the eluted DNA and 5) purification of the PCR product to obtain the ssDNA aptamer pool via PAGE. A counter selection step was also carried out after the fifth round using functionalized electrodes prepared the same way without target in order to eliminate any nonspecific DNA that binds to the gold surface as well as the linkers.

As explained above, our goal is to develop a label-free based selection protocol. However, here, we used a fluorescent labelled primer for amplification in order to validate the method by comparing the recovery obtained using both electrochemical and fluorescence techniques. Obviously, this method can be applied with unlabeled DNA for any target analyte.

Figure 4A:
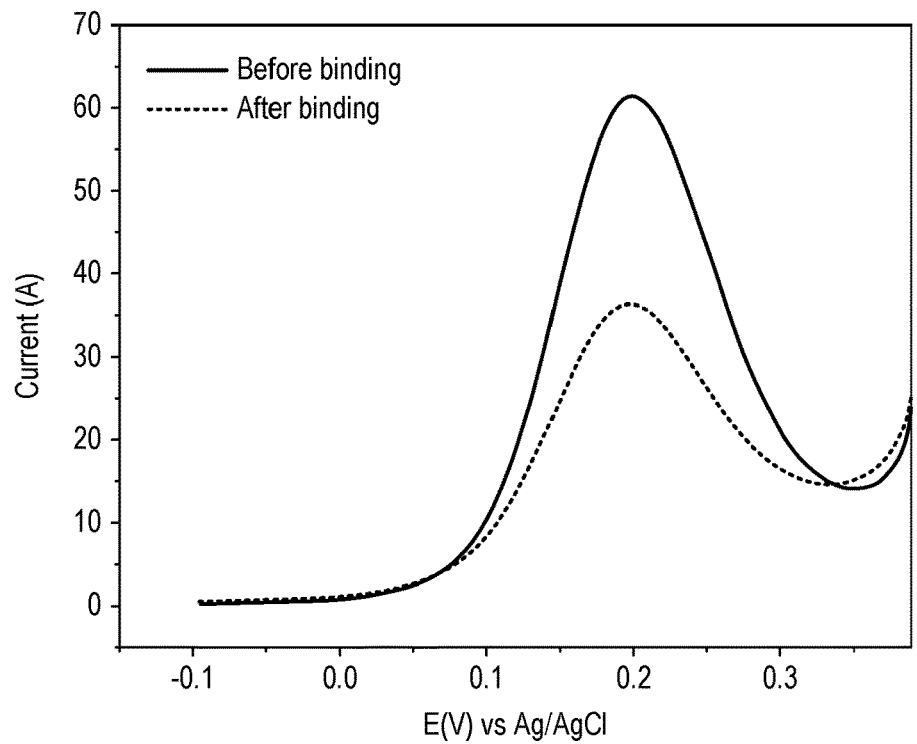
FIG. 4A shows representative example of square wave voltammograms of the 11DCL-modified electrodes in 5 mM $[Fe(CN)_6]^{4-/3-}$ redox solution in PBS, pH 7.4 before (black curve) and after binding with the DNA pool (red curve).
Figure 4B:
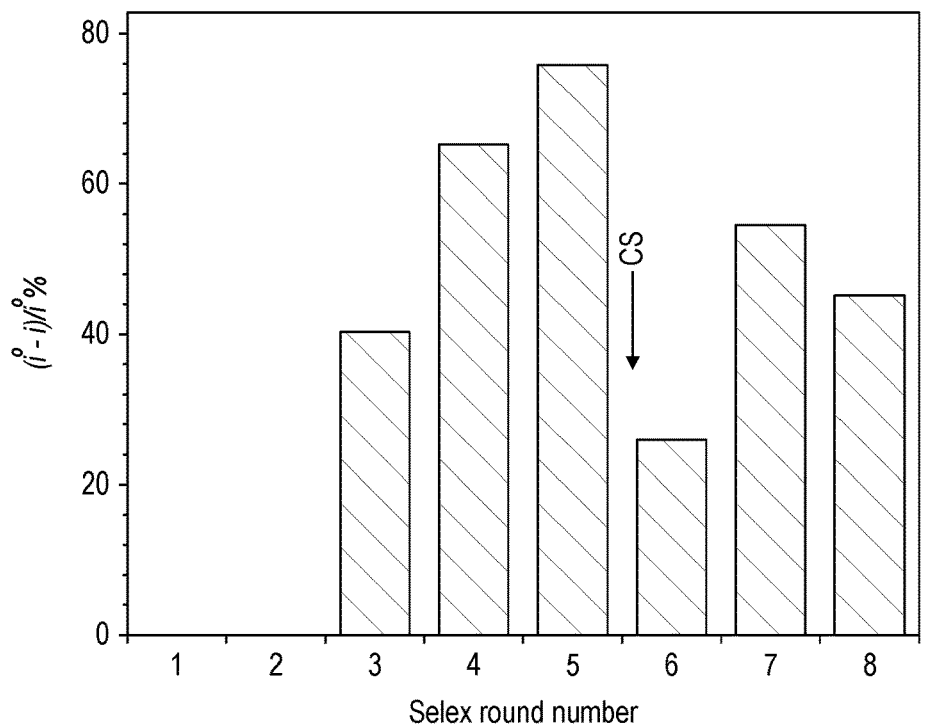
FIG. 4B shows Binding of ssDNA pools to 11-DCL after each SELEX cycle monitored by calculating the % change in the reduction peak current (($i^°-i$)/$i^°$ %) of the 11-DCL electrodes after binding with the DNA.

To monitor the progress of the SELEX and evaluate the enrichment process after each cycle, we measured the SWV reduction peak current of the electrodes in ferro/ferricyanide redox couple before and after incubating the electrodes with the DNA pool. FIG. 4A, shows a representative example of the SWV reduction peaks of the electrodes before and after incubation with the DNA. The binding of the target modified electrodes with the DNA leads to a drop in the peak current. This is attributed to the shielding effect of surface with the DNA as well as the negatively charges of the DNA phosphate backbone which hinders the access of the redox anion to the surface and retards the electron transfer. FIG. 4B shows the binding recovery evaluated by calculating the percentage change in the peak current $(i°-i)/i°$ % for each cycle. As can be seen in the Fig, no decrease in the current was obtained in the first two cycles indicating the very low amount of bound DNA to the surface. However, after that, a progressive increase in the $(i°-i)/i°$ % was seen implying the enrichment of the specific sequences. After counter selection the recovery was diminished due to the removal of the non-specifically bound sequences to the target. Then, in the subsequent rounds, the recovery increased significantly again suggesting sufficient enrichment in the specific aptamer pool.

Therefore, the selection was stopped and the DNA pool from round 8 was cloned, then 15 white colonies were randomly picked up for sequencing. The sequences were then identified and analysed by the multiple sequence alignment program PRALINE (Simossis, Kleinjung et al. 2005) (FIG. 7). Several other SEQ ID NO's: 14-17 are shown in alignment and due to space constraint have been shown as 9, 5, 4 and 25 in the figure.

Figure 5A:
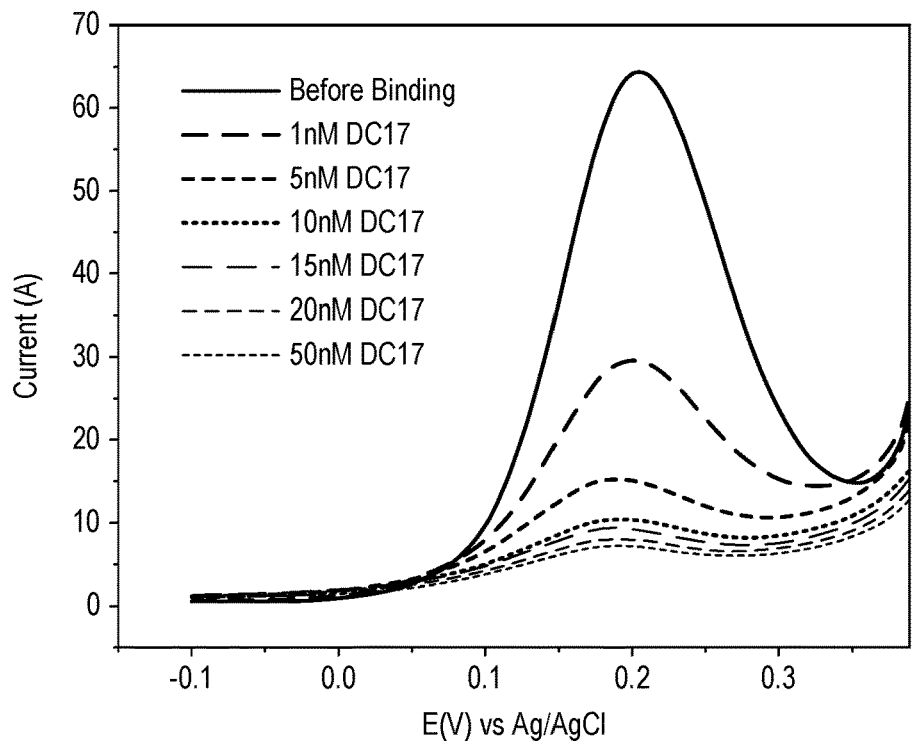
FIG. 5A shows Square wave voltammograms of the 11DCL-modified electrodes in 5 mM $[Fe(CN)_6]^{4-/3-}$ redox solution in PBS, pH 7.4 before and after binding with different concentrations of DC17 aptamer ranging from 1 nM to 50 nM.
Figure 5B:
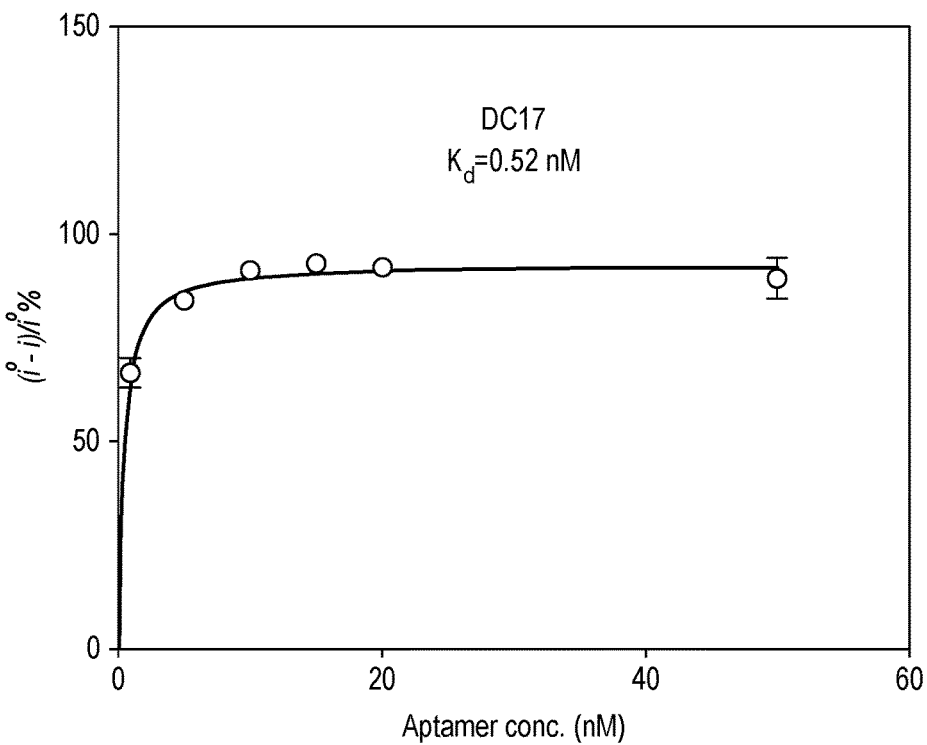
FIG. 5B shows electrochemical binding curve of 11-DCL to DC17 aptamer (a plot of the aptamer concentration versus ($i^°-i$)/$i^°$ %). The error bars represent the standard deviation obtained from duplicate measurements.

Determination of the dissociation constants of the selected aptamers: In order to evaluate the binding affinity of the selected aptamers, the $K_d$s of the aptamers were determined using SWV assay. After performing sequence alignment analysis of the aptamers, the sequences were grouped and 11 aptamers (SEQ ID NO's: 3-13 respectively—DC 3, 28, 7, 13, 19, 21, 27, 15, 17, 23 and 14) were chosen for the binding analysis testing. The SWV binding assay was performed using unlabeled aptamers after eliminating the primer binding sites. The assay was performed by incubating the hormone-modified electrodes with different concentrations of each aptamer (from 1 to 50 nM). After incubation, the electrodes were washed and subjected to SWV measurements in ferro/ferricyanide redox solution. The binding was then evaluated as the percentage decrease in the reduction peak current $(i° 4)/i°$ % upon binding of the electrodes with the aptamer. FIG. 5A shows a representative example of the SWV reduction peak current of the hormone electrode before and after binding with increasing concentrations of aptamer SEQ ID NO: 11-DC17. A significant decrease in the current was observed upon incubation with higher concentrations of the aptamer due to the negative charge of the DNA as explained above. We then plotted the binding affinity curves for each aptamer as the percentage change in the current versus the DNA concentration and the $K_d$s were calculated by nonlinear regression analysis of the curves. FIG. 5B shows a representative example of the binding curve of SEQ ID NO: 11-DC17. A shown in Table 1, the aptamers have shown very high affinity to the 11-DCL hormone target with $k_d$s in the sub- to low nanomolar range (from 0.52 to 38 nM). These results indicate the success of our protocol.

Application of the selected aptamer in voltametric competitive biosensor: As shown in Table 1, aptamer SEQ ID NO: 11 DC 17 showed the lowest $K_d$ and thus the highest affinity to the target. Hence, we selected this aptamer to develop an aptasensor for the detection of 11-DCL.

TABLE 1

| Sequence number | Aptamer sequence | $K_d$ (nM) |
|---|---|---|
| SEQ ID NO: 3 DC3 | CCGAGCATACTTAAACCATACTACAGTGTACCACTGGCAAAACCATTGATCCGCGAGCTC | 3.5 |
| SEQ ID NO: 4 DC28 | CACACGACGAAGGACCTATAACACCGTACAGCAATCGACACTTAGTAGACACCGCGGCCA | 3.5 |
| SEQ ID NO: 5 DC7 | GCGAAGCCCTCAACGAACAACACAGATCTAGATCTTTATGGTAAGGTCCGTGCTGCCC | 5.4 |
| SEQ ID NO: 6 DC13 | TGCGAAGCCCTCAACGAACAACACAGATCTAGATCTTTATGGTAAGGTCCGTGCTGCCC | 5.5 |
| SEQ ID NO: 7 DC19 | ACACGCACGAGTTCGTACAAAGAGACAAGATCAGCATAAAACCAAGACGGACGCCAACCA | 11.87 |
| SEQ ID NO: 8 DC21 | ATCAGTCGGACCGGCGGTAGAAGAGGAGTTCTATCACCAAAGGGAAAAGTAGTCAGCCG | 12.8 |
| SEQ ID NO: 9 DC27 | AGGGAGCCAAGACAGCGCAATAATTTCTGCAGTGTGGAGCTTTGTTTAATTTAGTTGTTA | 24.3 |
| SEQ ID NO: 10 DC15 | ATTACAGGAACGGGGACAAGGGCGAATAGAAATTGTGAAACATAAAGTCACGGGGTATGG | 38.12 |
| SEQ ID NO: 11 DC17 | TAACAGACGTCTCCCAAGCCATGAAAATTAGCCCAACTCATAGGACCATAACGCCCTACC | 0.52 |
| SEQ ID NO: 12 DC23 | TTCATGGCAACTGGGTAAGTTACTTTCACAATCCACTTCTAATATGATCGATCAGGCGCGG | 1.94 |
| SEQ ID NO: 13 DC14 | AGTGAGGAACACATAACCGCGTAACGGGTAGCTTACAAGGGCTATTGGGGATGCAAAGG | 2.10 |

The aptasensor is based on a competitive assay where a competition is established between the free analyte in the solution and immobilized analyte on the electrode surface for a fixed concentration of aptamer added to the solution. When the aptamer alone is added to the hormone modified electrode (aptasensor), a significant drop in the SWV reduction peak signal is obtained. Whereas, adding increasing concentrations of the analyte would lead to less available aptamer molecules bind to the electrode surface and thus, a less current change would be obtained as shown in Table 1.

Figure 6A:
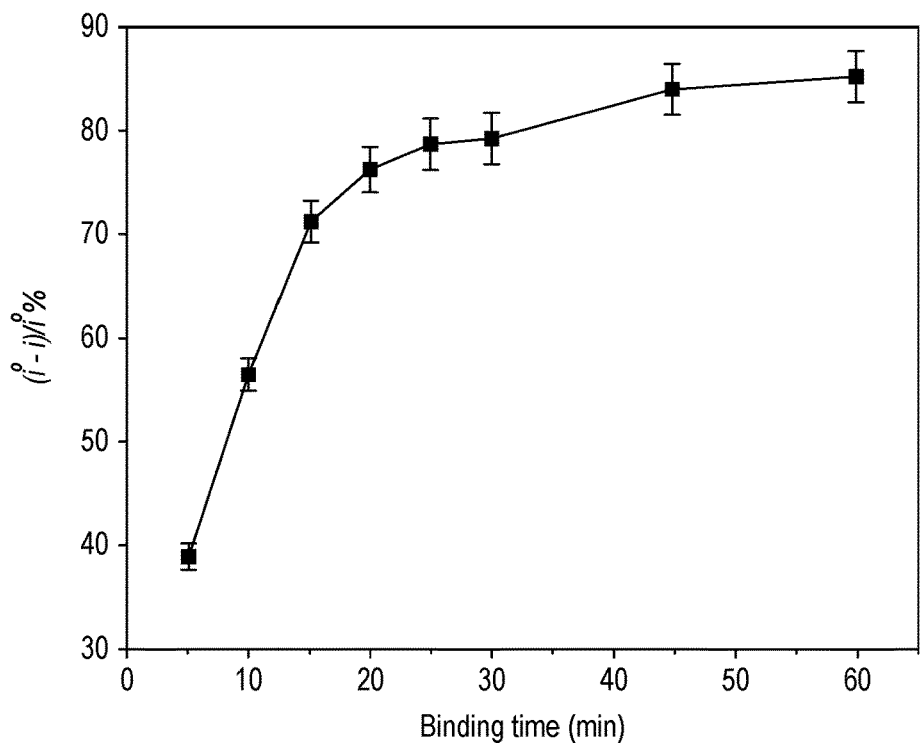
FIG. 6A shows the effect of incubation time on the aptamer/analyte binding (a plot of the current change (($i^°-i$)/$i^°$ %) after incubating the 11-DCL electrode with 5 µM aptamer at different time points (5-60 min).

With the aim to obtain the optimum sensor response, we first optimized the binding time of the aptamer and hormone. FIG. 6A shows the % change in the reduction current before and after incubating with 5 nM aptamer at different time points from 5-60 min. As shown in the figure, the peak current continued to decrease with increasing the incubation time until it reached plateau at almost 20 min Therefore, 20 min were chosen for the further experiments.

The concentration of the aptamer is also important in the competitive assay because low concentration of aptamer can lead to decreased sensor response and very high concentration would lead to low sensitivity. Therefore, from FIG. 5B, 5 nM aptamer was chosen for the competitive assay.

Figure 6B:
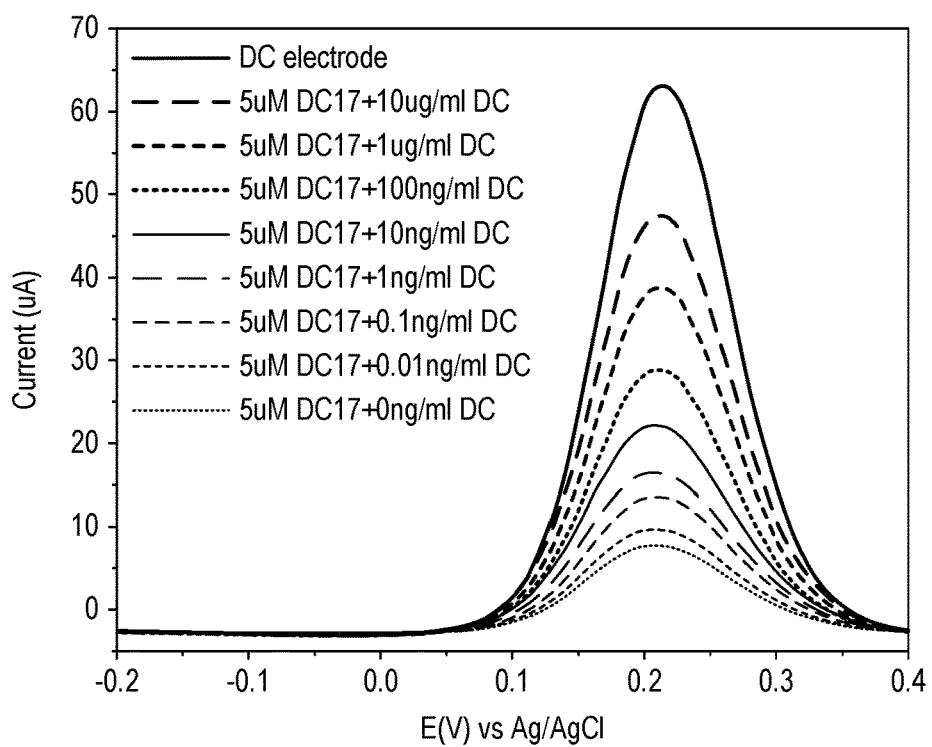
FIG. 6B Square wave voltammograms of the 11-DCL electrode before and after incubation with different concentrations of 11-DCL mixed with 5 nM of DC17 aptamer.
Figure 6C:
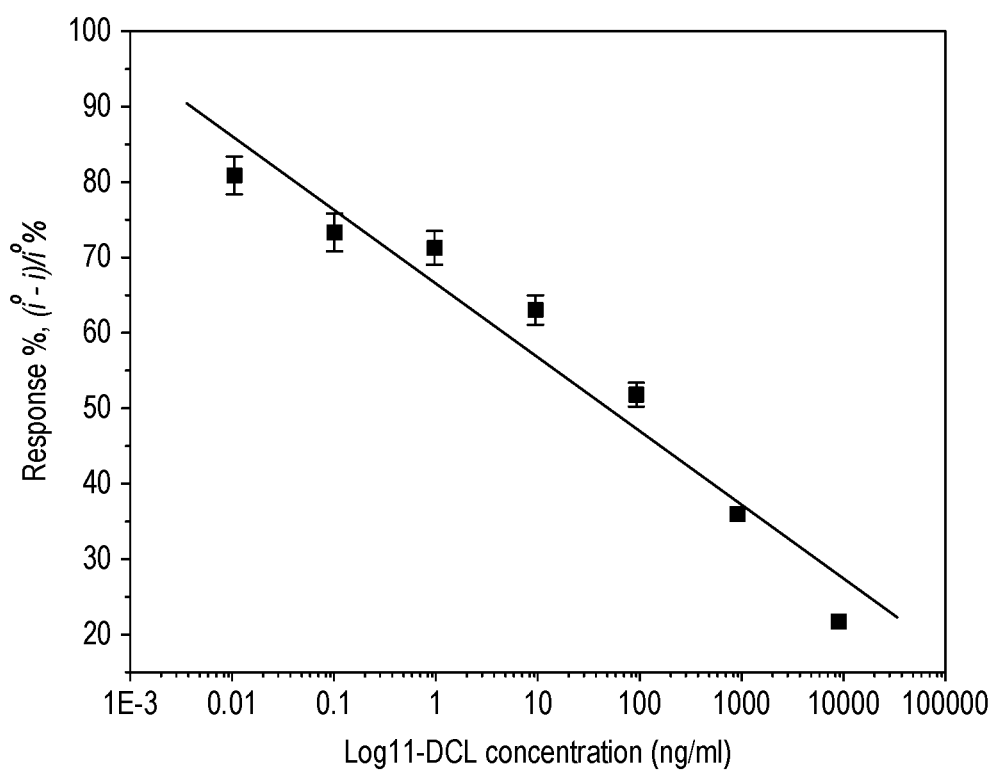
FIG. 6C the calibration curve for 11-DCL, plot of analytical response ($i^°-i_p$)/$i_o$ %) vs. logarithm of the 11-DCL concentration. The error bars represent the standard deviation of two repetitive measurements.

FIG. 6B shows the decrease in the SWV reduction peak upon incubation of the sensor with different concentrations of the hormone (from 0.01 ng/ml to 10 µg/ml) mixed with 5 nM of the aptamer DC17. The sensor response was calculated as the percentage change in the current $(i°-i_p)/i_o$ % where, i° is the current of the 11-DC before any incubation and $i_p$ is the current after incubation with different concentration of the analyte mixed with the aptamer. As shown in FIG. 6C, the calibration curve of the aptasensor plotted as the sensor response versus the logarithm of the hormone concentration exhibited a linear response. As the concentration of the analyte in the sample increases, the sensor response decreases due to the competition leading to less available aptamers that bind to the electrode. The linear regression equation of the calibration plot is: $(i°-i_p)/i°$ %=67.5-11.07 log $C_{11-DCL}$ [ng/mL] and correlation coefficient (R) of 0.982. The limit of detection of the aptasensor was calculated as the concentration corresponds to the difference between the mean blank signal (signal at zero analyte concentration) and 3 times the standard deviation of the blank. The LOD of the aptasensor was 11 pg/ml, indicating very high sensitivity of our method. This LOD is much lower than that obtained using commercial ELISA kit (0.34 ng/ml). This high sensitivity is attributed to the high binding affinity of the selected aptamer.

Figure 6D:
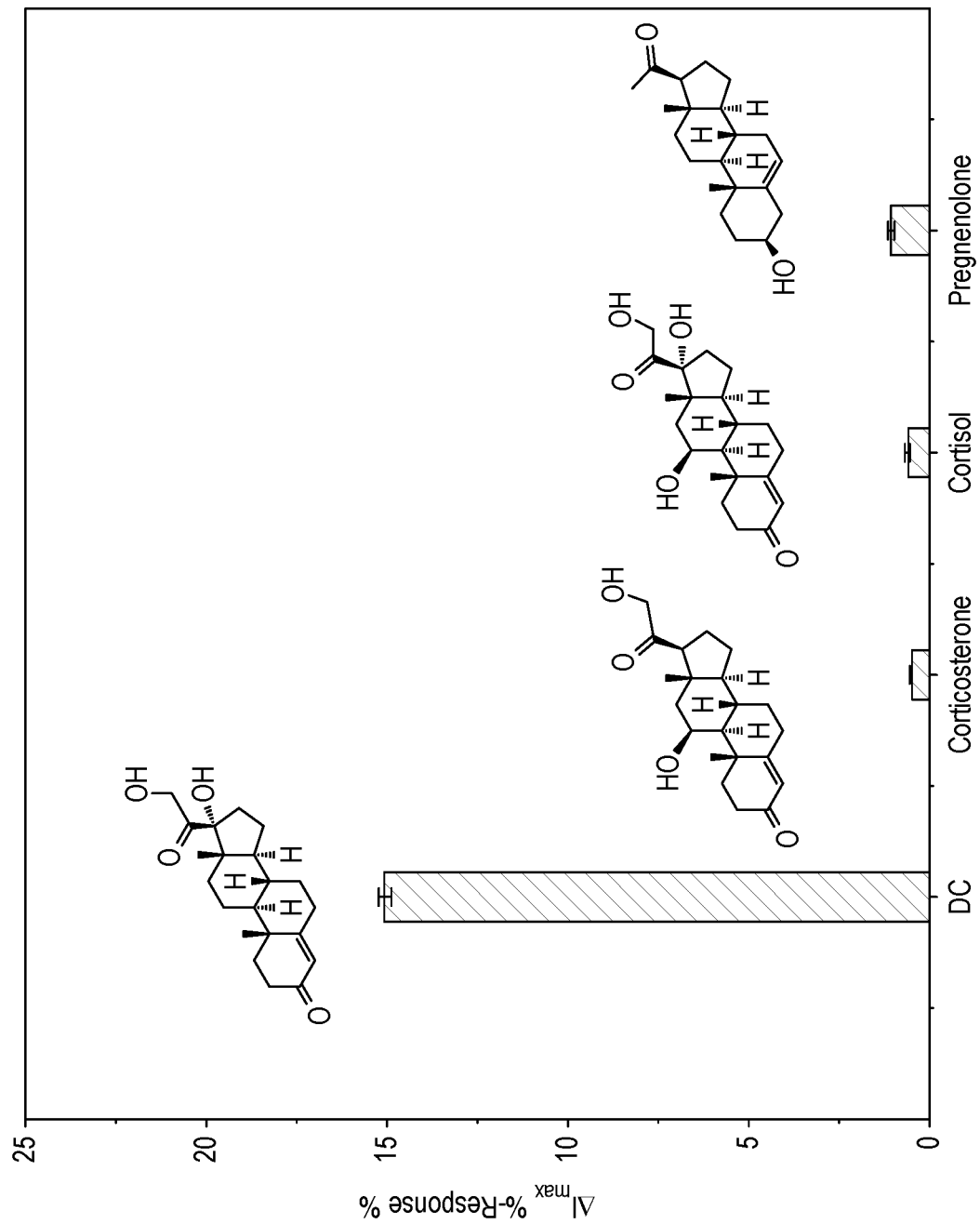
FIG. 6D Comparison of the response of the aptasensor to 1 ng/ml 11-DCL, cortisol, corticosterone or pregnenolone. The chemical structures of the hormones are shown.

Cross reactivity study of the aptasensor with other steroids analogues: In order to investigate whether the selected aptamer binds to other steroid hormones which have similar chemical structures such as cortisol, corticosterone and pregnenolone, we have incubated the aptasensor with the aptamer mixed with 1 ng/ml of each analogue instead of 11-DCL. The response here is calculated as the % change in the current at zero analyte ($\Delta i_{max}$)–the % response signal in each case. FIG. 6D shows high signal for 11-DCL compared with non-significant response obtained with the other analogues. This indicates high degree of selectivity of our aptamer towards 11-DCL. This could be attributed to the presence of the hydroxyl moiety in the hydrophobic core of the cortisol, corticosterone and pregnenolone molecules which created some hydrophilic nature that was not favourable for the aptamer binding unlike the non-hydroxylated core part of the 11-DCL molecule (Yang, Chun et al. 2017).

What is claimed is:

1. An electrochemical screening method for an aptamer, comprising:
   immobilizing a target analyte on an electrode by the following steps:
   a) coating an electrode with a cysteamine hydrochloride to create a cysteamine-modified electrode, wherein the electrode is made of a metal;
   b) washing the cysteamine-modified electrode with an ethanol to remove an unbound cysteamine hydrochloride from the cysteamine-modified electrode;
   c) adding a cross linker 1, 4-phenylene diisocyanate to an amine group of cysteamine hydrochloride on the surface of the cysteamine-modified electrode;
   d) washing with a methanol to remove any unbound cross linker 1, 4-phenylene diisocyanate from the surface of the cysteamine-modified electrode; and
   e) incubating the cysteamine-modified electrode in a 11-deoxycortisol solution for crosslinking the-target analyte and 11-deoxycortisol molecule on the surface of the cysteamine-modified electrode to create a 11-deoxycortisol-modified electrode to perform an electrochemical selection of an aptamer, wherein the aptamer is selected from a group consisting of a SEQ ID NO: 3-DC 3, SEQ ID NO: 4-D 28, SEQ ID NO: 5-DC 7, SEQ ID NO: 6 DC-13, SEQ ID NO: 7 DC-19, SEQ ID NO: 8 DC-21, SEQ ID NO: 9 DC-27, SEQ ID NO: 10 DC-15, SEQ ID NO: 11 DC-17, SEQ ID NO: 12 DC-23 and SEQ ID NO: 13 DC-14.

2. The method of claim 1, further comprising:
   using a synthetic single stranded DNA oligonucleotide sequence to be incubated with the 11-deoxycortisol-modified electrode; measuring the square wave volatmmetry reduction peak current of the electrode in a ferro/ferricyanide redox solution;
   binding the single stranded DNA oligonucleotide sequence to the 11-deoxycortisol modified electrode by immersing in binding buffer; washing the electrode and measuring the square wave volatmmetry reduction current after binding;
   eluting a bound single stranded DNA from the 11-deoxycortisol-modified electrode using an eluting buffer;
   repeating binding and eluting steps multiple times to collect a single stranded eluted DNA sequence; and
   performing a polymerase chain reaction on the eluted single stranded DNA sequence to obtain a DNA product.

3. The method of claim 2, further comprising:
cloning the DNA product on a specific vector and grown in an agar plates;
selecting a single colony of and growing overnight in a liquid media for a colony to grow;
performing polymerase chain reaction to amplify a single stranded DNA insert using M13 forward and M13 reverse primers sites inside the specific vector to make the aptamer; and
sequencing the aptamers obtained after amplification and aligning using specific software.

4. The method of claim 3, further comprising:
performing a binding analysis using the electrochemical screening method for 11-deoxycortisol with the aptamer.

5. The method of claim 1, wherein the aptamer is SEQ ID NO: 11 DC-17 aptamer.

6. The method of claim 1, wherein the metal is gold.

* * * * *

SEQUENCE LISTING

<160> NUMBER OF SEQ ID NOS: 17

<210> SEQ ID NO 1
<211> LENGTH: 18
<212> TYPE: DNA
<213> ORGANISM: Artificial Sequence
<220> FEATURE:
<223> OTHER INFORMATION: Forward 5' Primer

<400> SEQUENCE: 1
ataccagctt attcaatt                                                 18

<210> SEQ ID NO 2
<211> LENGTH: 18
<212> TYPE: DNA
<213> ORGANISM: Artificial Sequence
<220> FEATURE:
<223> OTHER INFORMATION: 3' PRIME PRIMER

<400> SEQUENCE: 2
agatagtaag tgcaatct                                                 18

<210> SEQ ID NO 3
<211> LENGTH: 60
<212> TYPE: DNA
<213> ORGANISM: Artificial Sequence
<220> FEATURE:
<223> OTHER INFORMATION: 11- DECORTISOL SEQUENCE

<400> SEQUENCE: 3
ccgagcatac ttaaaccata ctacagtgta ccactggcaa aaccattgat ccgcgagctc   60

<210> SEQ ID NO 4
<211> LENGTH: 60
<212> TYPE: DNA
<213> ORGANISM: Artificial Sequence
<220> FEATURE:
<223> OTHER INFORMATION: 11- DECORTISOL SEQUENCE

<400> SEQUENCE: 4
cacacgacga aggacctata acaccgtaca gcaatcgaca cttagtagac accgcggcca   60

<210> SEQ ID NO 5
<211> LENGTH: 58
<212> TYPE: DNA
<213> ORGANISM: Artificial Sequence
<220> FEATURE:
<223> OTHER INFORMATION: 11 DECORTISOL SEQUENCE

<400> SEQUENCE: 5
gcgaagccct caacgaacaa cacagatcta gatctttatg gtaaggtccg tgctgccc     58

<210> SEQ ID NO 6
<211> LENGTH: 59
<212> TYPE: DNA
<213> ORGANISM: Artificial Sequence
<220> FEATURE:
<223> OTHER INFORMATION: 11 DECORTISOL SEQUENCE

<400> SEQUENCE: 6
tgcgaagccc tcaacgaaca acacagatct agatctttat ggtaaggtcc gtgctgccc    59

<210> SEQ ID NO 7
<211> LENGTH: 60
<212> TYPE: DNA
<213> ORGANISM: Artificial Sequence

```
<220> FEATURE:
<223> OTHER INFORMATION: 11 DECORTISOL SEQUENCE

<400> SEQUENCE: 7
acacgcacga gttcgtacaa agagacaaga tcagcataaa accaagacgg acgccaacca      60

<210> SEQ ID NO 8
<211> LENGTH: 59
<212> TYPE: DNA
<213> ORGANISM: Artificial Sequence
<220> FEATURE:
<223> OTHER INFORMATION: 11 DECORTISOL SEQUENCE

<400> SEQUENCE: 8
atcagtcgga ccggcggtag aagaggagtt ctatcaccaa agggaaaagt agtcagccg       59

<210> SEQ ID NO 9
<211> LENGTH: 60
<212> TYPE: DNA
<213> ORGANISM: Artificial Sequence
<220> FEATURE:
<223> OTHER INFORMATION: 11 DECORTISOL SEQEUNCE

<400> SEQUENCE: 9
agggagccaa gacagcgcaa taatttctgc agtgtggagc tttgtttaat ttagttgtta     60

<210> SEQ ID NO 10
<211> LENGTH: 60
<212> TYPE: DNA
<213> ORGANISM: Artificial Sequence
<220> FEATURE:
<223> OTHER INFORMATION: 11 DECORTISOL SEQUENCE

<400> SEQUENCE: 10
attacaggaa cggggacaag ggcgaataga aattgtgaaa cataaagtca cggggtatgg     60

<210> SEQ ID NO 11
<211> LENGTH: 60
<212> TYPE: DNA
<213> ORGANISM: Artificial Sequence
<220> FEATURE:
<223> OTHER INFORMATION: 11 DECORTISOL SEQEUNCE

<400> SEQUENCE: 11
taacagacgt ctcccaagcc atgaaaatta gcccaactca taggaccata acgccctacc     60

<210> SEQ ID NO 12
<211> LENGTH: 61
<212> TYPE: DNA
<213> ORGANISM: Artificial Sequence
<220> FEATURE:
<223> OTHER INFORMATION: 11 DECORTISOL SEQUENCE

<400> SEQUENCE: 12
ttcatggcaa ctgggtaagt tactttcaca atccacttct aatatgatcg atcaggcgcg     60
g                                                                     61

<210> SEQ ID NO 13
<211> LENGTH: 60
<212> TYPE: DNA
<213> ORGANISM: Artificial Sequence
<220> FEATURE:
<223> OTHER INFORMATION: 11 DECORTISOL SEQUENCE

<400> SEQUENCE: 13
```

-continued

```
agtgaggaac acataaccgc gtaacgggta gcttacaagg gctattgggg gatgcaaagg        60

<210> SEQ ID NO 14
<211> LENGTH: 60
<212> TYPE: DNA
<213> ORGANISM: Artificial Sequence
<220> FEATURE:
<223> OTHER INFORMATION: 11 DECORTISOL SEQUENCE

<400> SEQUENCE: 14
caccgatgct acagtaccac ccagttacat accccgtct cacactaacg atgcgcccga         60

<210> SEQ ID NO 15
<211> LENGTH: 60
<212> TYPE: DNA
<213> ORGANISM: Artificial Sequence
<220> FEATURE:
<223> OTHER INFORMATION: 11 DECORTISOL SEQUENCE

<400> SEQUENCE: 15
tagagaactc agcgaacatt tgctgtcaat ggggtcaagc gtaaacaatc caagggtgta        60

<210> SEQ ID NO 16
<211> LENGTH: 59
<212> TYPE: DNA
<213> ORGANISM: Artificial Sequence
<220> FEATURE:
<223> OTHER INFORMATION: 11 DECORTISOL SEQEUNCE

<400> SEQUENCE: 16
gaacgtactt cccgaacctt acttacgatt ttttacacaa gtgagcccg ctaatccgc          59

<210> SEQ ID NO 17
<211> LENGTH: 60
<212> TYPE: DNA
<213> ORGANISM: Artificial Sequence
<220> FEATURE:
<223> OTHER INFORMATION: 11 DECORTISOL SEQEUNCE

<400> SEQUENCE: 17
agggagccaa gacagcgcaa taatttctgc agtgtggagc tttgtttaat ttagttgtta       60
```